United States Patent [19]

MacDonald, III et al.

[11] 4,200,169
[45] Apr. 29, 1980

[54] STETHOSCOPE

[75] Inventors: Robert D. MacDonald, III, Stillwater; Frederick W. Nelson, Cottage Grove, both of Minn.

[73] Assignee: Minnesota Mining and Manufacturing Company, Saint Paul, Minn.

[21] Appl. No.: 951,375

[22] Filed: Oct. 16, 1978

[51] Int. Cl.² ............................................. A61B 7/02
[52] U.S. Cl. .................................. 181/131; 181/135
[58] Field of Search ........................ 181/131, 137, 135

[56] References Cited

U.S. PATENT DOCUMENTS

| | | | |
|---|---|---|---|
| 1,847,607 | 3/1932 | Hardt | 181/131 |
| 3,108,652 | 10/1963 | Littmann | 181/131 |
| 3,168,161 | 2/1965 | Littmann | 181/135 |
| 3,437,172 | 4/1969 | Allen | 181/131 |
| 3,504,760 | 4/1970 | Littmann | 181/135 |
| 3,570,625 | 3/1971 | Allen | 181/131 |

Primary Examiner—Stephen J. Tomsky
Attorney, Agent, or Firm—Cruzan Alexander; Donald M. Sell; Carolyn A. Bates

[57] ABSTRACT

This invention relates to a stethoscope having improved acoustical properties. The improvement comprises twin, smooth-walled sound pathways extending from the chestpiece to the ear tips which are free of sound leakage and each pathway has a constant diameter along its entire length.

10 Claims, 8 Drawing Figures

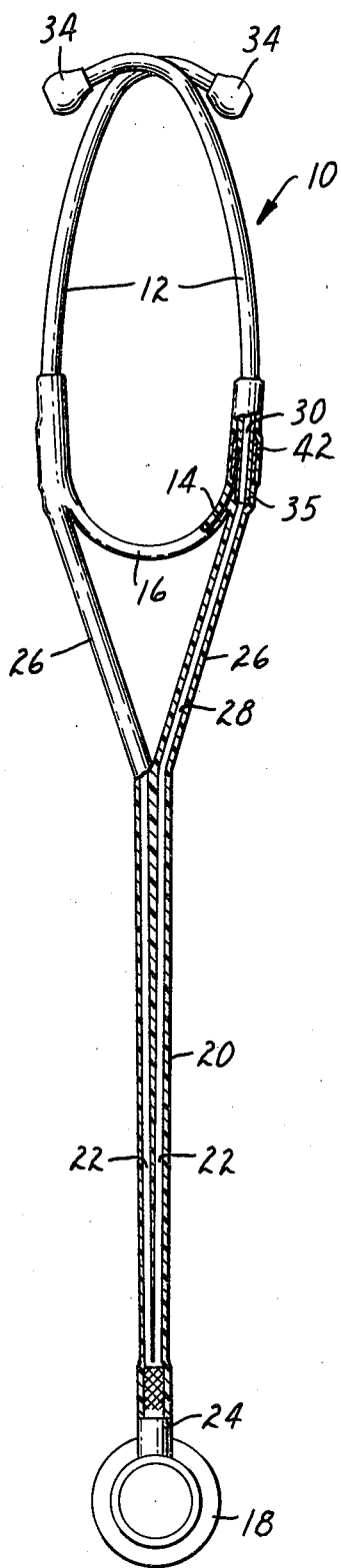
FIG.1
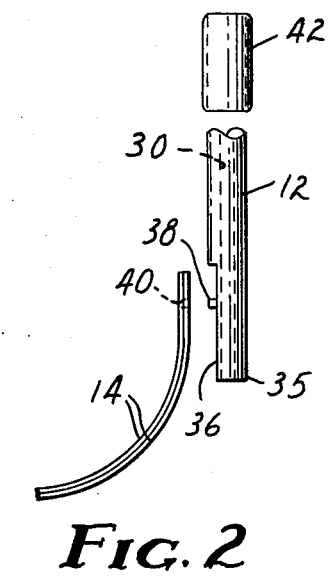
FIG.2
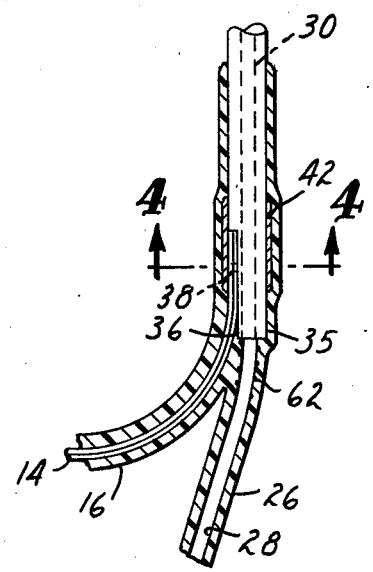
FIG.3
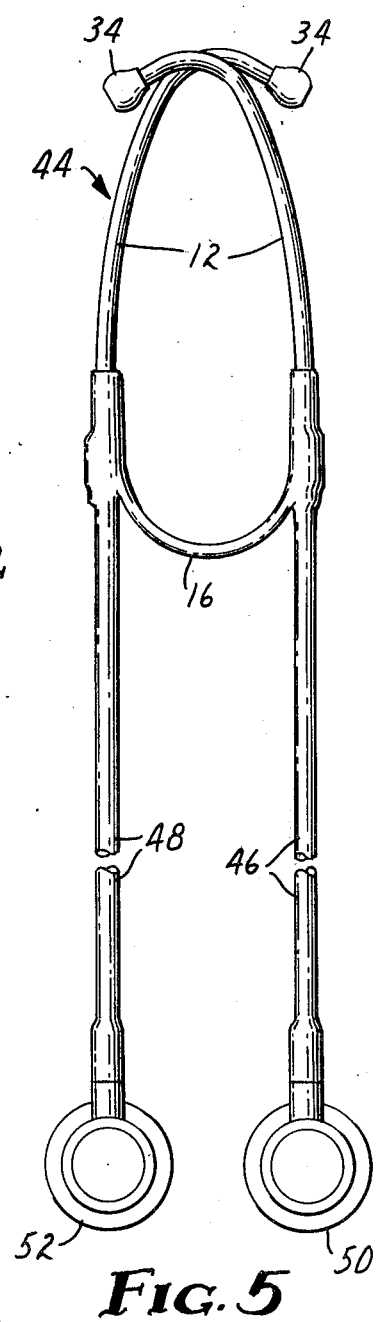
FIG.4
FIG.5

STETHOSCOPE

This invention relates to stethoscopes and more particularly to an improved binaural stethoscope.

Medical stethoscopes generally consist of a chestpiece for picking up sounds and a headpiece for transmitting sounds from the chestpiece to the ears of the wearer. The headpiece commonly comprises a flexible tube connected to the chestpiece, a Y or T junction to provide a separate passageway to each ear, and ear tubes for taking the sound to each ear. The ear tubes have traditionally consisted of metal tubes, appropriately bent, which carry the sound; earpieces which provide some cushioning for the wearer and a measure of insulation against outside sound sources; and a tensioning device, such as a spring, which holds the ear tubes in such a relationship that they can be spread apart to be put on, but will then stay in the wearer's ears comfortably when the device is being used. Stethoscopes of the general type described above are illustrated, for example, in U.S. Pat. Nos. 3,108,652 and 3,275,099.

Many of the stethoscopes available today are simple, light-weight and generally provide a high level of audio performance. However, for some purposes, particularly for heart studies by cardiologists, there is a need for a stethoscope having even greater audio-sensitivity. When one is listening for blood flow, for valves opening and closing, and for turbulence around promotories or constructions in vessels, etc., the highest audio performance is needed.

In general, stethoscopes of the prior art have failed to provide maximum sensitivity due in part to degradation of the acoustic signal between the chestpiece and the ear tube and/or leakage of sound from one or more points in the air passageway between the chestpiece and the ear tube.

Degradation of the acoustic signal occurs wherever there are steps or constrictions in the walls of the acoustic pathway, e.g., where the sound passes through nipples connecting the flexible tubing and the metal parts of the stethoscope. Sound leakage may also occur at these junctions, particularly when the flexible tubing is made of rubber which tends to crack with age.

Numerous attempts have been made by the prior art to produce stethoscopes having improved acoustical properties. For example, U.S. Pat. No. 3,437,172 (Allen) discloses a stethoscope having: (1) dual air columns extending between the the microphone and ear tubes; and (2) the binaural coupling spring molded into the tubing wall. The dual air columns are alleged to improve transmission of higher frequences by avoidance of mismatched impedances which occur in a single tube stethoscope. Molding the binaural coupling spring into the wall of the Y-coupling tube by a dip-coating process eliminates an obstruction in the air passage, thereby suggesting a further improvement in acoustical quality.

Although the stethoscope described by Allen appears to have some improvements over stethoscopes known at the time of his disclosure, it suffers from certain disadvantages. Firstly, the sound waves must pass through a "dog leg" bend in the air column as it bifurcates a short distance from the chestpiece. In all of the embodiments illustrated, except that of FIG. 5, there is a right-angled bend in the sound tube at the fork of the Y. Even in the embodiment of FIG. 5, the sound waves must pass through a significant curve in the tubing before reaching the ear tube. Such curves and bends, particularly, right-angle bends, result in sound degradation.

Other stethoscopes have utilized dual air columns to improve acoustic properties. For example, a stethoscope sold under the tradename Sprague-Rappaport (Hewlett-Packard) uses two tubes of heavy rubber to connect a chromium-plated chestpiece to a stylish headpiece. This device suffers from the same drawbacks discussed above in connection with the Allen stethoscope. Additional disadvantages include: (1) the use of rubber tubing which deteriorates with age; and (2) the rubber is relatively floppy causing the dual tubes to move about and bang into each other thereby giving rise to background noise and extraneous sounds.

The present invention provides an acoustic stethoscope exhibiting markedly improved ability to hear weak and/or complex sounds compared to stethoscopes of the prior art. In particular, the stethoscope of the present invention is designed for use by cardiologists in the study of heart sounds and in differentiating between very subtle changes in sound associated with various heart conditions.

The improved stethoscope according to the invention comprises: a pair of conventional elongated rigid ear tubes having upper ends suitably curved for insertion into the ears of the wearer and lower ends connected to flexible connecting tubing; at least one chestpiece having an adapter for attachment of the flexible connecting tubing, flexible tubing connecting the chestpiece to the ear tubes; and at least one elongated U-shaped leaf spring having end portions interconnecting the ear tubes at the lower ends thereof for biasing the ear tubes toward each other. The flexible connecting tubing defines a pair of separate passageways extending from the chestpiece to the ear tubes with one of the passageways being connected to, and co-extensive with, one ear tube and the other passageway being connected to, and co-extensive with, the other ear tube thereby providing separate acoustical passages to each ear. The specific improvement associated with the stethoscope of the present invention resides in the feature of having separate acoustical passages each having smooth interior walls of substantially constant diameter throughout its length from the chestpiece to the upper end of the ear tube.

The preferred embodiment of the invention is a stethoscope in which the pair of passageways formed in the flexible tubing are molded side-by-side in a one-piece construction for a major portion of the distance between chestpiece and ear tubes. The passageways must, of course, bifurcate eventually to allow them to connect to the ear tubes. However, the bifurcation is preferably accomplished with as little deviation from a straight-line path as possible. This is accomplished by deliberately making the passageways non-parallel so that they gradually diverge as they progress from the chestpiece to the ear tubes.

The diameter of the acoustic pathways formed by the flexible tubing and the rigid ear tubes is substantially constant throughout the distance between the chestpiece and the upper ends of the ear tubes, e.g., there is no constriction in the pathway or significant disturbance in its wall caused by a junction between the flexible tubing and the ear tube. In prior art devices, the flexible tubing is simply press fitted over the end of the ear tube. This requires that the diameter of the ear tube be smaller than the diameter of the flexible tubing thus creating a step-like disruption in the wall of the acoustic pathway. Such departures from smooth wall construction will degrade the acoustic signal. A further disadvantage of prior art stethoscopes wherein the flexible tubing is simply press-fitted over the end of the ear tube is that sound leakage can occur at such junctions.

The stethoscope of the present invention provides dual smooth-walled acoustic pathways free of sound leakage by forming the flexible tubing in situ over the lower ends of the ear tubes by a dip-coating process. Although dip-coating is known in connection with stethoscope tubing, (See, for example, U.S. Pat. No. 3,437,172) it is believed to be heretofore unknown to dip-coat the lower ends of the ear tubes with plastic to form a leak proof junction between ear tube and flexible tubing.

The acoustic stethoscope of the present invention exhibits markedly improved ability to hear weak or complex sounds compared with stethoscopes of the prior art. It does this by reducing signal degradation between pick-up (chestpiece) and earpiece by using a constant-diameter, leak-free sound conducting tube all the way from the pick-up to the ear. Furthermore, by using a separate tube from pick-up to ear for each ear, signal degradation at junctions and bifurcations is avoided. Still further, twinning the tubes from pick-up to ears for as long a distance as practical, by forming them as a one-piece molding side-by-side from pick-up to ear tubes results in a remarkable reduction in background noise and enables the user to differentiate between sounds that have been barely detectable with stethoscopes heretofor. It is suspected that this effect, which is surprisingly large, may be caused by a variety of factors, such as: increased sound-carrying capacity of the twinned tube over the conventional single tube due to its sturdier shape causing less general background sound generation; and elimination of highly distracting noise, bangs, clicks and subsequent echoes caused by tubes touching each other characteristic of some two-tube designs of the prior art.

A second embodiment of the invention is a "differential" stethoscope. In this embodiment, the two tubes from the earpieces are not brought together to form a single twinned tube, but remain separate and connect to two separate chestpieces. By this construction, the advantages of a single twinned tube are lost, but the advantages of the sealed construction and the smooth internal passages remain. In addition, one can place the chestpieces at different locations on the body and listen to the sound of events as heard from different angles or through different intervening structures. Or one can hear, for example, material flowing through different parts of a vessel.

DESCRIPTION OF THE DRAWINGS

Further understanding of the invention will be facilitated by reference to the accompanying drawing wherein:

FIG. 1 is a face view of the preferred embodiment of the stethoscope of the invention partially broken away and shown in section;

FIG. 2 is an exploded front view of the junction between the leaf spring and the ear tube of the stethoscope of FIG. 1;

FIG. 3 is a transverse sectional view of the junction between the leaf spring, ear tube and flexible tubing of the stethoscope of FIG. 1;

FIG. 4 is a sectional view taken along line 4—4 of FIG. 3;

FIG. 5 is a face view of a stethoscope showing double chestpieces;

As illustrated in FIGS. 1, 2 and 3 stethoscope 10 comprises a pair of ear tubes 12 secured together by a prestressed leaf spring 14 optionally enclosed in tubing 16. A conventional chestpiece 18 is attached to ear tubes 12 by elongated flexible tubing 20 which contains dual air passages 22 which run side-by-side within a common structure of flexible plastic tubing such as polyvinyl chloride for a major portion of the distance between chestpiece 18 and ear tubes 12. In the lower end of tubing 20 which attaches to chestpiece 18, passages 22 merge into a single passage adapted to be coupled to a single fitting 24 of an appropriate chestpiece. The upper end of tubing 20 bifurcates into coupling arms 26, each of which attaches to one of the ear tubes 12. The air passages 22 are continued as air passages 28 in the coupling arms which are in turn continued as air passages 30 in the ear tubes 12.

Figure 6:
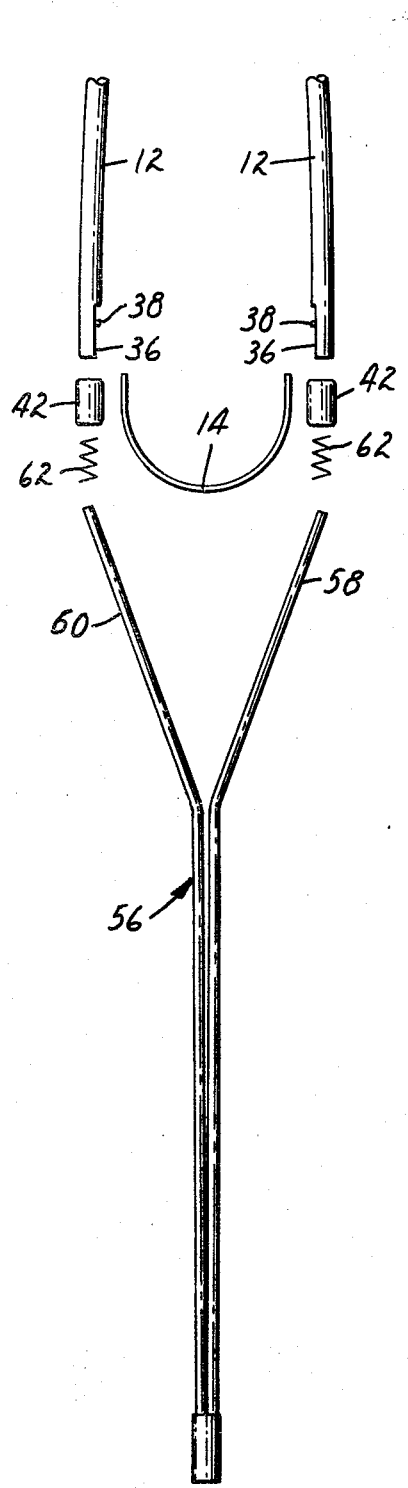
FIG. 6 is an exploded face view of the head set portion of the stethoscope of FIG. 1 immediately before dip-coating illustrating the mandrel used to form the flexible tubing.

It is an object of the present invention to maintain the twin air passages as straight as possible throughout the distance between the chest piece and the ear tips. For this reason, passages 22 are not parallel but gradually diverge toward the ear tubes thus avoiding sharp bends in the tubing.

Binaural ear tubes 12 are typically made of a metal such as aluminum, stainless steel, or brass, plated if desired, and have upper ends suitably curved toward each other to allow insertion into the ears of the wearer. Ear tips 34, which are generally made of a soft and somewhat pliable material such as plastics or rubbers, (e.g., Delrin or silicone), are attached to the upper ends of ear tubes 12 to provide cushioning for the ears and also to insulate the ears against outside sounds. The lower end portions 35 of ear tubes 12 extend into the respective coupling arms 26 of flexible tubing 20, and an air-tight junction is formed between air passages 28 of coupling arms 26 and air passages 30 of the respective ear tubes to which they are joined.

Lower end portions 35 of the ear tubes 12 may be indentically formed as illustrated in FIGS. 2 and 3. The exterior wall of one side of end portion 35, which is circular in cross section as illustrated in FIG. 4, is milled down to form a flat surface 36 to which leaf spring 14 is attached. Surface 36 contains a pin 38 in the center portion thereof which is aligned with hole 40 in the tip of the leaf spring to prevent the ear tube from rotating. A bushing 42 is then force fitted down over the end of the ear tube and the leaf spring to permanently attach them together. It is important to note that the bushing is not crimped or deformed in any way after it is forced down over the leaf spring as is generally done in prior art stethoscopes utilizing a bushing to attach the leaf spring to the ear tube. Crimping the bushing results in constriction of the air passage in the ear tube. As was previously discussed, any abrupt change in the diameter of the air passage results in sound degradation and is avoided by the present invention. Accordingly, the air passage 30 of the ear tube remains essentially circular in cross-section even after the bushing is force fitted into place as is illustrated in FIG. 4.

Although a stethoscope having a single leaf spring is illustrated, it is also contemplated that a double leaf spring arrangement similar to that illustrated in U.S. Pat. Nos. 3,168,161 or 3,504,760 may be used.

The chestpiece 18 may be any appropriate chestpiece having high acoustical quality. Sound is commonly picked up at the chestpiece by two devices, the diaphragm and the bell. The diaphragm is regarded as better for picking up higher frequency sounds and the bell is preferred for the lower frequencies. The bell is bascially an open cup which is placed over the desired spot on the body and the diaphragm is similar but with a membrane or diaphragm stretched over the mouth of the cup. The detailed design of chestpieces has been the subject of much variation, for the purpose of maximizing the useful audio information that can be collected. Various shapes and configurations are known. Combination chestpieces which can be used in either mode are common (U.S. Pat. No. 3,951,230) and are preferred in the present invention.

FIG. 5 illustrates a differential stethoscope according to the invention in which the ear tubes and leaf spring arrangement is identical to that shown in FIGS. 1-4. Instead of the twin passages in a single structure construction as shown in FIG. 1, stethoscope 44 of FIG. 5 has two flexible tubes 46 and 48 which are separate from each other along the entire length from chestpiece to ear-tube. Each of the tubes 46 and 48 is attached by adapter means to chestpieces 50 and 52, respectively.

It is also contemplated that the tubes 46 and 48 of the differential stethoscope may be joined in a common structure along a portion of their length. However, such a construction would require longer tubing and is less preferred for that reason.

The differential stethoscope, employing two chestpieces, is particularly useful in listening to sounds which are generated by organs which are reproduced on both sides of the body, such as the lungs. Using segmental auscultation techniques one can compare the sounds of one lung with those of the other. Since lung disease is generally patchy, rarely occuring uniformly in one lung, or especially across both lungs, one is able to detect such disease by noting differences in sound between one side and the other, for example by noting differences in pitch, amplitude and phase between the sounds. Alternatively, one can compare sounds in a patient being examined with sounds from a known standard, such as a natural or synthesized healthy sound. Similar considerations are applicable to listening to sounds in vessels (e.g. arteries) in different limbs, whereby differences in the sounds of the arrival of blood pulses can indicate the status of the blood supply to the area.

A key feature of the stethoscope of the present invention is that the air passage through which sound is transported from the chestpiece to the upper end of the ear tube is of substantially constant diameter throughout its length. Prior to the present invention, air passages in stethoscopes contained a change in diameter at the junction between the flexible tubing and the ear tubes. This change was due to the fact that the flexible tubing had to be stretched over the end of the ear tube thus requiring that the diameter of the bore in the flexible tubing be larger than the diameter of the lower end of the ear tube.

In the stethoscope of the present invention the flexible tubing is not press-fitted over the end of the ear tube. Rather, the flexible tubing is formed in situ by a dip-coating process resulting in a smooth transition in the internal wall of the air passage between the flexible tubing and the ear tubes. A most significant feature, in addition, is that the whole unit is completely sealed from ear to chestpiece. There are no loose fittings or movable parts. The potential for leaks is thereby eliminated.

The dip-coating process itself is not novel. It is widely used for coating articles with a layer of protective material including vinyl plastics. Its use in fabricating the flexible tubings of stethoscopes is also known. It is used in the manufacture of currently available stethoscopes, such as those sold under the trademark "Littmann" by the 3M Company. The procedure is also specifically mentioned in U.S. Pat. No. 3,437,172, column 3, lines 73 et seq.

A feature of dip-coating is the ability to introduce the coating material in its liquid state (e.g., polyvinyl chloride plastisol before curing) into intimate contact with the article to be coated. The coating material can reach small shapes and recesses, and can conform accurately to small changes in dimension, intentional or unintentional, in the article to be coated. The coating is, therefore, particularly valuable when one wishes to encase an article with a material which will seal it efficiently from the outside. One obtains a seal, after curing, which has been formed around every contour of the article being sealed—and not, for example, a seal which relies on a press fit in a springy material or on a grip from a stretched elastic material. Dip-coatings are, therefore, desirable to effect an audio-leak-proof coupling between the ear tubes and the flexible tubes of stethoscopes.

Although dip-coating processes have heretofore been used to form the flexible tubing of stethoscopes and to encase the leaf spring, it is believed that prior to the present invention, stethoscope ear tubes have not been dipped into the liquid plastic to form a permanent and leak-proof junction between the ear tubes and the flexible tubing.

Figure 7:
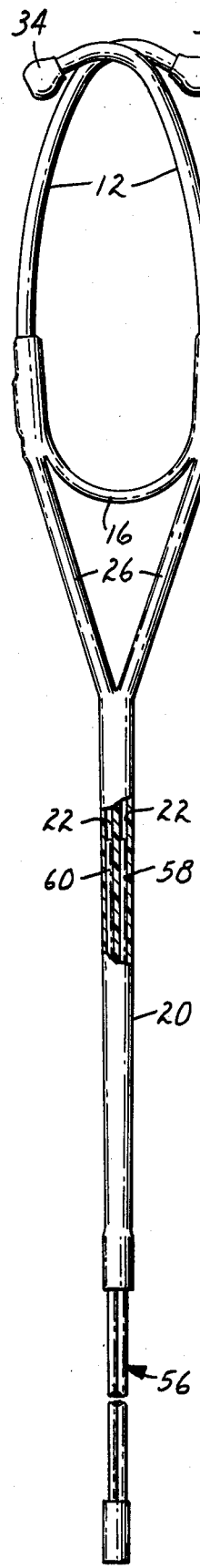
FIG. 7 is a face view of the head set portion of the stethoscope of FIG. 1 immediately after dip-coating, illustrating removal of the mandrel, partially broken away and shown in section.
Figure 8:
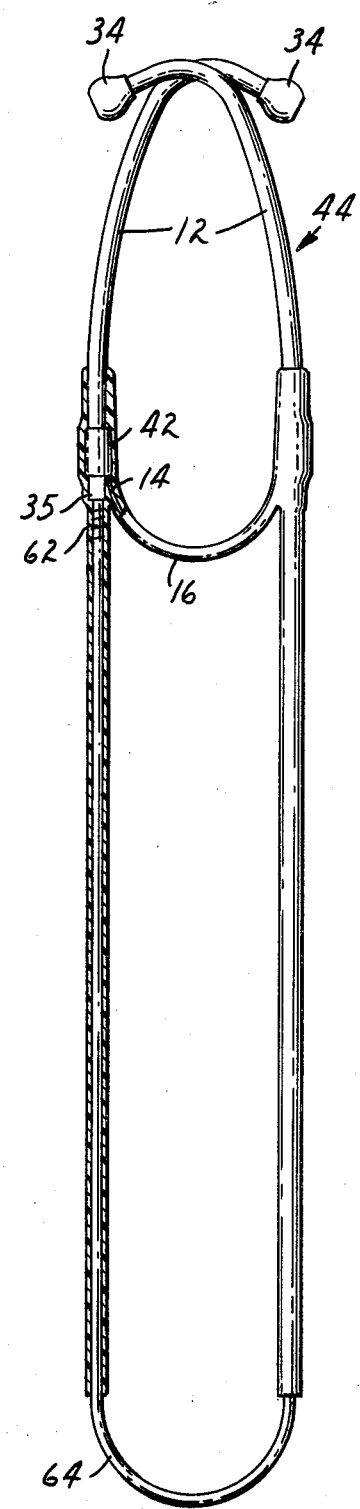
FIG. 8 is a face view of the stethoscope of FIG. 5 after dip-coating prior to removal of the mandrel, partially broken away and shown in section.

The actual proces of performing a dip-coating procedure is an art rather than a science. One skilled in the art will recognize that a number of variables enter into the obtaining of a specific coating. These variables include the composition of the plastic being used; the temperatures of the articles being coated and the mandrels being used, and their heat capacities; the curing cycle used; and so on. The overall procedure in this instance, however, is to assemble the ear tubes 12, with the leaf spring 14 positioned and the arms 58 and 60 of a mandrel 56 inserted into the lower ends of the ear tubes as illustrated in FIGS. 6 and 8. Anti-kink springs 62 may be optionally used just below the junction between ear-tube and flexible tube, to provide a measure of strain relief at this point in the finished article (useful for example if the instrument is casually folded up and thrust into a pocket). The assembly is dipped into a vinyl plastisol to a depth such that the entire junction between mandrels and ear tubes is entirely immersed. The dipped assmbly is then withdrawn from the plastisol, bearing a coating which is subsequently fully cured, e.g., in an oven. The mandrel is then withdrawn from the assembly as illustrated in FIG. 7, leaving smooth-bore tubing where it had been coated with plastic. Appropriate trimming and finishing operations are then done, e.g., to the lower end of the new twin tube.

The complete process of dip-coating is summarized in the following eight steps:

1. Place the anti-kink springs (if used) on the mandrel arms.
2. Insert one mandrel into each ear tube.
3. Place the headset-mandrel assembly into an oven for preheating.
4. Remove the headset-mandrel assembly and dip it to the desire level (just over the headset bushings) in PVC.
5. Remove the assembly from the liquid PVC and return it to the oven.
6. Remove the assembly from the oven and cut the chestpiece end of the tubing off exposing the end of the mandrel.
7. Pull the mandrel out of the plastic, thereby forming the lumen of the tubing.
8. Finish trim the chestpiece end of the tubing.

The process variables include the type of plastic, time and temperature of the preheat, dipping time, and the time and temperature of the oven curing. The surface finish of the lumen of the tube is dependent on the surface finish of the mandrel. The wall thickness is determined by the curing rate of the plastic and the amount of heat in the mandrel. The amount of heat in the mandrel is determined by the preheat temperature, the cross-sectioned area of the mandrel and the heat capacity of the mandrel material.

The key to dipping the headset is smooth mandrels which fit exactly into the lumen of the ear tube. The plastic will conformably coat the mandrel forming an uninterrupted transition from plastic to metal for the sound waves. Additionally, the heatset will be sealed when manufactured and won't loosen up and leak sound during use.

FIG. 8 illustrates the mandrel 64 used in the dip coating fabrication of the differential stethoscope of FIG. 5.

Fabrication of the stethoscopes of the invention is further illustrated by reference to the following Example.

EXAMPLE 1

The coating material, Plastisol Blending Resin (Lakeside Plastics Inc., Oshkosh, Wisconsin) is plasticized with a mixture of dioctyl phthallate (25%) and Santicizer 160 (Monsanto) (75%) in a ratio (plastisol:plasticizer) of 50:50 and is held in a suitable tank at a temperature of about 80° F. The tooling mandrels, for example the mandrel/ear tube assembly shown in FIG. 6, or in FIG. 8, are preheated to 300°-400° F. and then are dipped into the tank of liquid plastisol to a depth such that the junction between the mandrels of the ear tubes are appropriately immersed. The coated assembly is withdrawn and is transferred to a drying oven at 300°-400° F. The resin cures over a 5-10 minute period to give a smooth, shiny external finish. The mandrels are removed, leaving the cured resin as the flexible tubular body of a stethoscopic headset.

What is claimed is:

1. In a stethoscope comprising a pair of elongated rigid ear tubes each having an upper end suitably curved for insertion into the ear of the wearer, a lower end for attaching to flexible tubing and a central passageway extending lengthwise therethrough having a diameter, at least one chestpiece having an adapter for attachment to flexible tubing, flexible tubing acoustically connecting the at least one chestpiece to said ear tubes and spring means attached to said lower end of said ear tubes for biasing said ear tubes toward each other, the improvement wherein said flexible tubing defines separate twin passages extending between the at least one chestpiece and said ear tubes, each of said passages being connected to and continuous with one of said ear tube passageways by a leak-free junction and the diameter of said passages being equal to the diameter of said ear tube passageways thereby forming twin air columns having constant diameters extending between the at least one chestpiece and the upper ends of said ear tubes.

2. The stethoscope according to claim 1 wherein said twin passages are side-by-side in a common structure for a major portion of their length.

3. The stethoscope according to claim 2 wherein said twin passages diverge along their length from said chestpiece to said ear tubes.

4. The stethoscope according to claim 1 wherein said flexible tubing is attached to a single chestpiece.

5. The stethoscope according to claim 1 wherein the at least one chestpiece consists of two chestpieces.

6. The stethoscope according to claim 1 wherein said diameter of said bore through said ear tubes has a circular cross-section throughout its length.

7. The stethoscope according to claim 1 wherein said spring means comprises at least one elongated leaf spring prestressed to form a U-shaped arc and securing means interengaging said leaf spring at its ends to said ear tubes.

8. The stethoscope according to claim 7 wherein the portion of the surface of said lower end of said ear tube which interengages said leaf spring is smooth and flat and contains a pin therein for aligning with a hole in said leaf spring so that when so aligned, rotation of ear tubes with respect to said leaf spring is prevented.

9. The stethoscope according to claim 8 wherein said securing means comprises a bushing.

10. The stethoscope according to claim 1 further comprising flexible earpieces attached to the upper end of said ear tubes to provide a cushion between said ear tubes and the ears of the wearer.

* * * * *